United States Patent [19]

Baudouin et al.

[11] 4,225,497
[45] Sep. 30, 1980

[54] PREPARATION OF N-SUBSTITUTED OLIGO-IMIDES

[75] Inventors: Michel Baudouin, Saint-Fons; Jean Abblard, Saint-Didier Au Mont D'or, both of France

[73] Assignee: Rhone-Poulenc Industries, Paris, France

[21] Appl. No.: 8,053

[22] Filed: Jan. 31, 1979

Related U.S. Application Data

[63] Continuation-in-part of Ser. No. 931,676, Aug. 7, 1978.

[30] Foreign Application Priority Data

Feb. 19, 1978 [FR] France .................. 78 36383

[51] Int. Cl.$^2$ ............................................. C07D 207/44
[52] U.S. Cl. .................... 260/326.5 FM; 260/326 R; 260/326 C; 260/326 E; 260/326 S; 260/326 NS; 260/326 H; 260/326 HL; 260/326.26; 260/326.27; 260/326.5 B; 546/256; 546/272; 546/281; 548/143; 548/153; 548/181; 548/193; 548/267; 548/328; 528/170; 528/345
[58] Field of Search .............................. 528/170, 345; 260/326.26, 326 N, 326.27, 326.50, 326.5 FM

[56] References Cited

U.S. PATENT DOCUMENTS

| | | | |
|---|---|---|---|
| 3,025,300 | 3/1962 | Heubner | 260/326 N |
| 3,406,148 | 10/1968 | Sambeth et al. | 528/170 |
| 3,669,930 | 6/1972 | Asahara et al. | 528/170 |
| 3,671,490 | 6/1972 | Bargain | 528/322 |
| 3,729,510 | 4/1973 | Norton | 260/326 N |
| 3,732,188 | 5/1973 | Holub et al. | 528/345 |
| 3,732,189 | 5/1973 | Criwells et al. | 528/345 |
| 3,767,671 | 10/1973 | Klebe et al. | 260/326 N |
| 3,855,239 | 12/1974 | Crivello | 260/326.26 |
| 3,862,129 | 1/1975 | Kwiatkowski | 260/326.26 |
| 3,868,351 | 2/1975 | Hand et al. | 528/345 |
| 3,972,087 | 8/1976 | Freedman | 260/326 N |
| 3,996,203 | 12/1976 | Hand et al. | 528/345 |
| 4,118,392 | 10/1978 | Salbe et al. | 260/326 N |
| 4,125,535 | 11/1978 | Wolfon | 260/326 N |

Primary Examiner—Mary C. Lee
Attorney, Agent, or Firm—Burns, Doane, Swecker & Mathis

[57] ABSTRACT

N-substituted oligo-imides of the formula:

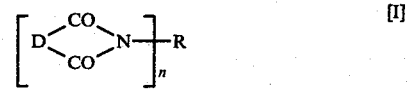

in which D represents a divalent radical selected from the group comprising:

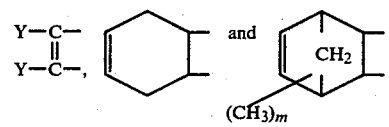

in which m is 0 or 1, Y is hydrogen, chlorine or methyl, n is a positive integer of 5 or less, and R is an organic radical of valency n, containing up to 50 carbon atoms, are prepared by reacting an anhydride of the formula:

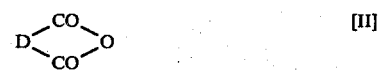

with an amine of the formula:

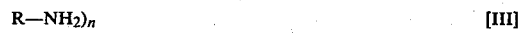

in which formulae D, R, and n as above defined, said reaction being carried out in the presence of a catalyst system comprising a mixture of a compound ($\alpha$) and a compound ($\beta$), being a strong inorganic or organic oxygen-containing acid and ($\beta$) being a salt of such acid with a cation selected from the group comprising pyridinium, quaternary phosphonium and tertiary sulfonium cations.

18 Claims, No Drawings

PREPARATION OF N-SUBSTITUTED OLIGO-IMIDES

CROSS-REFERENCE TO RELATED APPLICATION

This application is a continuation-in-part of our copending application, Ser. No. 931,676, filed Aug. 7, 1978.

SUMMARY OF THE INVENTION

The present invention relates to a process for the preparation of N-substituted oligo-imides from dicarboxylic acid anhydrides and an amine.

The N-substituted oligo-imides prepared according to the invention are, more especially, compounds of the formula:

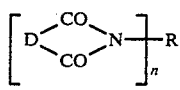  [I]

in which D represents a divalent radical selected from the group comprising:

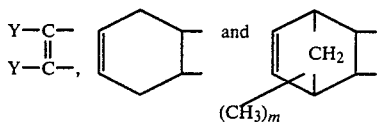

in which m is 0 or 1, Y is hydrogen, chlorine or methyl, n is a positive integer of 5 or less, and R is an organic group of valency n, containing up to 50 carbon atoms.

The radical R can be purely hydrocarbon in nature, or can contain one or more heteroatoms; the radical R can thus contain a plurality of hydrocarbon groups or heterocyclic rings joined or linked together by heteroatoms or heteroatomic groups; same can also contain substituents such as: halogen atoms and nitro, amino, hydroxyl, alkoxy and alkylthio groups, in addition, of course, to carbonyl groups.

The invention, particularly, relates to a process for the preparation of oligo-imides of the formula I, from an anhydride of the formula:

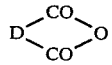  [II]

and an amine of the formula:

  [III]

in which formulae D, R and n are as above defined, the said process being characterized in that the reaction is carried out in the presence of a catalyst system comprising a mixture of a compound ($\alpha$) and a compound ($\beta$), ($\alpha$) denoting a strong inorganic or organic oxygen-containing acid and ($\beta$) denoting a salt of this acid, more especially a salt with a cation selected from the group comprising pyridinium-, phosphonium- and sulfonium cations.

DETAILED DESCRIPTION OF THE INVENTION

The parent application of the present application, Ser. No. 931,678, the disclosure of which in its totality is hereby incorporated by reference, discloses the preparation of oligo-imides of Formula I from an anhydride of Formula II, and an amine of Formula III in the presence of a catalyst system comprising a mixture of a strong inorganic or organic oxygen-containing acid (compound $\alpha$) and an ammonium salt thereof, wherein the ammonium is di-, tri- or tetrasubstituted on the nitrogen atom by organic groups. It has now been found that the oligo-imides of Formula I can be prepared according to the present invention in the presence of the above-defined catalyst mixture comprising the strong oxygen-containing acid and a salt thereof with an organic cation other than substituted ammonium.

By the term strong inorganic or organic oxygen-containing acid ($\alpha$), there is intended an oxygen-containing mono- or polyacid in which at least one of the acid functions possesses an ionization constant in water, pKa, which is 3 or less. Exemplary of acids of this type, there are mentioned: from among the inorganic acids, sulfuric, orthophosphoric and pyrophosphoric acids; from among the organic acids, organo-sulfonic acids, in particular para-toluenesulfonic, methanesulfonic and naphthalenesulfonic acids, organophosphonic acids, in particular monoalkyl- or monoaryl-phosphonic acids, such as methylphosphonic or benzenephosphonic acid, and strong mono- or polycarboxylic acids such as dihalogeno- and trihalogeno- (especially chloro- and fluoro-) -acetic or -propionic acids.

According to the invention, the organic sulfonic acids, and more particularly, alkyl- or aryl-sulfonic acids, such as methane sulfonic, para-toluenesulfonic and benzenesulfonic acids, are preferably employed as the strong acid ($\alpha$).

As the pyridinium salt ($\beta$), a salt is therefore used in which the anionic moiety corresponds to the acid ($\alpha$), [namely, the anionic moiety yields the acid ($\alpha$) by addition of the H$^+$ ions required for electrical neutrality] and in which the cationic moiety has the formula:

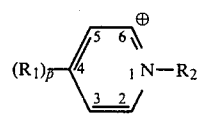  [IV]

wherein the substituents $R_1$ are the same or different from each other and represent straight or branched alkyl containing 1 to about 20 carbon atoms such as, for example, methyl, ethyl, n-propyl, iso-propyl, n-butyl, iso-butyl, t-butyl, n-pentyl, iso-pentyl, tertamyl, n-hexyl, n-heptyl, n-octyl, n-nonyl, n-decyl, n-undecyl, n-dodecyl, (the foregoing alkyl groups are unsubstituted or substituted by a halogen atom, nitro, or alkoxy containing 1 to 5 carbon atoms;

an alkoxy group as defined above; straight or branched alkenyl containing 1 to about 20 carbon atoms and 1 to about 10 ethylene double bonds such as e.g., vinyl, propene-1-yl, allyl, methyl-1-propene-2-yl, butene-1-yl, pentene-3-yl, hexene-2-yl, butadiene-1,3-yl, hexadiene-3,5-yl which are unsubstituted or substituted by alkoxy containing 1 to 5 carbon atoms;

a cycloalkyl or cycloalkenyl group containing 5 to 8 carbon atoms and, in the case of a cycloalkenyl group 1 or 2 ethylene double bonds, such as, for example, cyclopentyl, cyclohexyl, cycloheptyl, cyclohexene-1-yl, which are unsubstituted or substituted by 1–3 alkyl or alkoxy groups having 1 to 5 carbon atoms;

aryl, in particular phenyl, which is unsubstituted or substituted by 1 to 3 alkyl or alkoxy having 1 to 5 carbon atoms, as for example phenyl, tolyl, xylyl, mesityl;

arylalkyl, in particular phenylalkyl containing 1 to 5 carbon atoms in the alkyl group and 1 or 2 fused or non-fused benzene groups in the aryl moiety (the benzene nuclei are unsubstituted or substituted by 1 to 3 alkyl or alkoxy having 1 to 5 carbon atoms) as for example, benzyl, p-methylbenzyl, phenetyl, phenyl-3-propyl;

a halogen atom, as for example chlorine, bromine;

a functional group, as for example, hydroxyl, cyano, nitro, carboxy, alkylcarbonyloxy, alkoxycarbonyl, acyl;

p is an integer of from 0 to 5;

or one or two pairs of substituents $R_1$ wherein the 2 substituents $R_1$ are in ortho position relative to each other, form 1 or 2 unsaturated divalent groups of the formula:

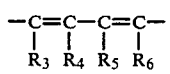  [V]

wherein $R_3$, $R_4$, $R_5$ and $R_6$, which may be the same or different from each other, each represent hydrogen, straight or branched alkyl, containing 1 to 5 carbon atoms which are unsubstitued or substituted by a halogen atom, nitro, or alkoxy containing 1 to 5 carbon atoms, an alkoxy group as defined above, a halogen atom, a functional group, such as hydroxyl, cyano, nitro, carboxy, alkylcarbonyloxy, alkoxycarbonyl, acyl;

$R_2$ represents:

hydrogen, an alkyl-, alkoxy-, alkenyl-, cycloalkyl-, cycloalkenyl-, aryl- or arylekyl-group as defined above within the definition of $R_1$, a functional group as defined above within the definition of $R_1$.

The term "pyridinium" therefore does not only denote the pyridinium cation itself, but also any other cations which include a pyridine nucleus wherein the nitrogen atom is positively charged such as, for example, quinolinium and acridinium cations. Quarternary pyridinium salts, that is, salts wherein $R_2$ is not hydrogen, are preferably used.

As examples of pyridinium ($\beta$) salts which are most particularly useful, there may be cited salts of 1-methylpyridinium, 1-methyl-2-vinylpyridinium, 1-methyl-3-hydroxypyridinium, 1-methyl-4-cyanopyridinium, 1-methyl-3,5-dichloropyridinium, 1,2,5-trimethylpyridinium, 1,2,4,6-tetramethylpyridinium, 1-ethylpyridinium, 1-ethyl-2-vinylpyridinium, 1-ethyl-2-ethoxypyridinium, 1,4-diethylpyridinium, 1-methyl-4-acetylpyridinium, 1-propylpyridinium, 1-propyl-4-phenylpyridinium, 1-butylpyridinium, 1-butyl-2,4-dimethylpyridinium, 1-butyl-2-vinylpyridinium, 1-methoxypyridinium, 1,4-dimethoxypyridinium, 1,3,5-trimethoxypyridinium, 1-vinylpyridinium, 1-phenylpyridinium, 1-benzylpyridinium, 1-benzyl-3-carboxypyridinium, 1-(p-methylbenzyl)pyridinium, 1-benzyl-3,5-dimethylpyridinium, 1-methylquinolinium, 1-ethylquinolinium, 1-vinylquinolinium, 1-allylquinolinium.

As a phosphonium ($\beta$), salt, there is also used a salt wherein the anionic moiety is an anion of an acid ($\alpha$) and the cationic moiety has the formula:

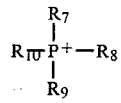  [VI]

wherein $R_7$, $R_8$, $R_9$ and $R_{10}$ represent identical or different organic radicals in which the free valency is borne by a carbon atom.

More specifically, $R_7$, $R_8$, $R_9$, and $R_{10}$ represent an alkylalkoxy-, alkenyl-, cycloalkyl-, cycloalkenyl-, aryl- or arylalkyl- as defined above within the definition of $R_1$.

Two of the substituents $R_7$, $R_8$, $R_9$ and $R_{10}$ together may form a single divalent substituent which is alkylene containing 4 to 6 carbon atoms or alkenylene containing 4 to 6 carbon atoms, and 1 or 2 ethylene double bonds; this divalent substituent is unsubstituted or substituted by 1–3 alkyl- or alkoxy groups containing 1 to 3 carbon atoms, as for example, tetramethylene, pentamethylene, hexamethylene.

The ($\beta$) salts which are used within the present invention are quarternery phosphonium salts.

Exemplary of phosphonium ($\beta$) salts which are most particularly useful the following may be cited: salts of tetramethylphosphonium, tetraethylphosphonium, tetrapropylphosphonium, tetrabutylphosphonium, tetra(-chloromethyl) phosphonium, tetraphenylphosphonium, tetrabenzylphosphonium, trimethylethylphosphonium, trimethylphenylphosphonium, trimethylbenzylphosphonium, triethylvinylphosphonium, triethylpropylphosphonium, triethyldecylphosphonium, triethylphenylphosphonium, triethylbenzylphosphonium, tripropylethylphosphonium, tripropylphenylphosphonium, tributylethylphosphonium, triphenylmethylphosphonium, triphenylethylphosphonium, triphenylpropylphosphonium, triphenylbutylphosphonium, triphenylbenzylphosphonium, tribenzylethylphosphonium, tri(p-methylphenyl)methylphosphonium, dimethylethylphenylphosphonium, dimethyloctylbenzylphosphonium, diethylmethylphenylphosphonium, dipropylmethylphenylphosphonium, dimethyldiethylphosphonium, dimethyldiphenylphosphonium, diethyldiphenylphosphonium, methylethylisopropylisobutylphosphonium, methylethylphenylbenzylphosphonium, phenylethyltetramethylenephosphonium, phenylpropyltetramethylenephosphonium, phenylethylpentamethylenephosphonium.

As sulfonium ($\beta$) salt, there is also used a salt wherein the anionic moiety is an anion of an acid ($\alpha$) and the cationic moiety has the formula

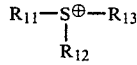  (VII)

wherein $R_{11}$, $R_{12}$, and $R_{13}$ represent identical or different organic radicals in which the free valency is borne by a carbon atom.

More specifically $R_{11}$, $R_{12}$ and $R_{13}$ represent an alkyl alkoxy, alkenyl, cycloalkyl, cycloalbenyl, aryl, or arylalkyl as defined above within the definition of $R_1$.

Two or three of the substituent $R_{11}$, $R_{12}$ and $R_{13}$ together may form a single divalent (in the case of two substituents combined together) substituent which is alkylene containing 4 to 8 carbon atoms or alkenylene containing 4 to 8 carbon atoms and 1 or more ethylenic double bonds; or a single trivalent substituent (in the case of 3 substituents combined together) which is saturated or unsaturated and contains 4 to 10 carbon atoms and in the case of an unsaturated group contains 1 or several ethylenic double bonds.

The sulfonium (β) salts which are used within the present invention therefore are tertiary salts.

As examples of sulfonium (β) salts which are most particularly used, the following may be cited: salts of trimethylsulfonium, triethylsulfonium, tripropylsulfonium, tributylsulfonium, triphenylsulfonium, tri(2-chloro-ethyl)sulfonium, dimethylvinylsulfonium, dimethylallylulfonium, dimethylbutylsulfonium, dimethylphenylsulfonium, dimethylbenzylsulfonium, diethylmethylsulfonium, diethylpropylsulfonium, diethylphenylsulfonium, dibutylbenzylsulfonium, dimethylcyclohexylsulfonium, diphenylmethylsulfonium, diphenylethylsulfonium, diphenylallylsulfonium, methylethylphenylsulfonium, methylethylbenzylsulfonium, methoxymethylphenylsulfonium.

The catalyst system (α)/(β) according to the invention is prepared by mixing a strong inorganic or organic acid (α) with the salt (β); they can be mixed together either before mixing them with the reactants, or in the reaction medium; of course, it is possible to use a catalyst system comprising several acids (α) and several salts (β); thus, if an acid (α) is mixed with a salt (β) derived from another acid (α'), and if these acids (α) and (α') have a similar acidity, an equilibrium will automatically be established in the reaction medium and a mixture of the acids (α) and (α') and their corresponding salts (β) and (β') will thereby be obtained.

Taking account of the meanings indicated previously for the symbol D, the anhydride can be, in particular, maleic anhydride, which is the preferred, chloromaleic anhydride, citraconic anhydride, tetrahydrophthalic anhydride or endomethylenetetrahydrophthalic anhydride.

When n is other than 1, the amine of the formula (III) is a polyamine which can be a diamine or a compound containing up to 5 primary amino groups.

Suitably, diamine compounds having the formula:

$$H_2N-E-NH_2 \qquad (VIII)$$

are used in which the symbol E represents a divalent radical containing from 2 to 30 carbon atoms. This radical can be, in particular, a linear or branched alkylene radical having fewer than 13 carbon atoms, a phenylene or cyclohexylene radical or a radical of the formula:

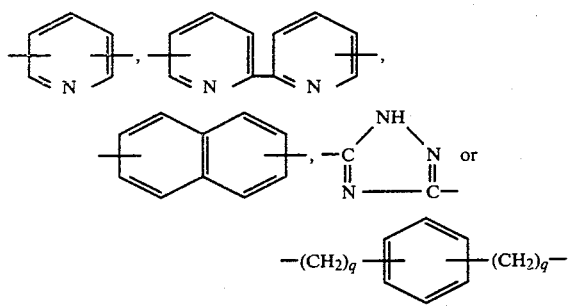

in which q represents an integer from 1 to 3. The symbol E can also include 2 to 5 phenylene or cyclohexylene radicals which are joined to one another by a single valence bond or by an inert atom or group such as —O—, —S—, an alkylene group having from 1 to 3 carbon atoms, —CO—, —SO$_2$—, —NR$_{14}$—, —N=N—, —CONH—, —COO—, —P(O)R$_{14}$—, —CONH—X—NHCO—,

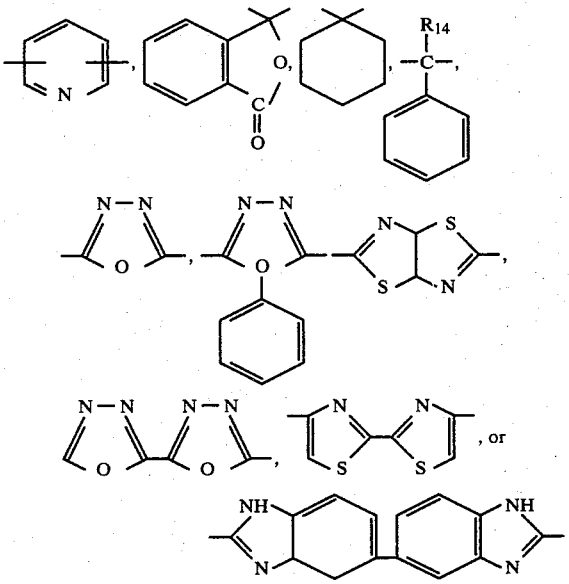

in which R$_{14}$ represents hydrogen, alkyl having from 1 to 4 carbon atoms, phenyl or cyclohexyl and X represents an alkylene group having fewer than 13 carbon atoms.

Exemplary of such diamines, the following may be cited: 4,4'-diaminodicyclohexylmethane, 1,4-diaminocyclohexane, 2,6-diaminopyridine, meta-phenylenediamine, para-phenylenediamine, 4,4'-diaminodiphenylmethane, 2,2-bis-(4-aminophenyl)-propane, benzidine, para-aminophenyl oxide, para-aminophenyl sulfide, 4,4'-diaminodiphenylsulfone, bis-(4-aminophenyl)-methylphosphine oxide, bis-(4-aminophenyl)-phenylphosphine oxide, bis-(4-aminophenyl)-methylamine, 1,5-diaminonaphthalene, meta-xylylenediamine, para-xylylenediamine, 1,1-bis-(para-aminophenyl)phthalane, hexamethylenediamine, 6,6'-diamino-2,2'-bipyridyl, 4,4'-diaminobenzophenone, 4,4'-diaminoazobenzene, bis-(4-aminophenyl)-phenylmethane, 1,1-bis-(4-aminophenyl)-cyclohexane, 1,1-bis-(4-amino-3-methylphenyl)-cyclohexane, 2,5-bis-(m-aminophenyl)-1,3,4-oxadiazole, 2,5-bis-(p-aminophenyl)-thiazolo-[4,5-d] thiazole, 5,5'-di-(m-aminophenyl)-bis-(1,3,4-oxadiazolyl-2,2'), 4,4'-bis-(p-aminophenyl)-2,2'-bithiazole, m-bis-[4-(p-aminophenyl)-thiazol-2-yl]-benzene, 2,2'-bis-(m-aminophenyl)-5,5'-dibenzimidazole, 4,4'-diaminobenzanilide,, phenyl 4,4'-diaminobenzoate, N,N'-bis-(4-aminobenzoyl)-p-phenylenediamine, 3,5-bis-(m-aminophenyl)-4-phenyl-1,2,4-triazole, 4,4'-N,N'-bis-(p-aminobenzoyl)-diaminodiphenylmethane, bis-p-(4-aminophenoxycarbonyl)-benzene, bis-p-(4-aminophenoxy)-benzene, 3,5-diamino-1,2,4-triazole, 1,1-bis-(4-aminophenyl)-1-phenylethane and 3,5-bis-(4-aminophenyl)pyridine. According to the invention, the aromatic diamines are the preferred.

Other than the bis-primary diamines, the polyamines of the formula (III) which are preferably used include those which have fewer than 50 carbon atoms and which possess from 3 to 5 —NH$_2$ groups per molecule. The —NH$_2$ groups can be borne by a benzene nucleus which is optionally substituted by methyl groups, or they can be borne by a naphthalene, pyridine or triazine nucleus; they can also be borne by several benzene nuclei which are joined to one another by a single valence bond or by an inert atom or group which can be one of those described above within the scope of the definition of the symbol E, or also

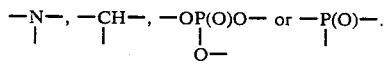

Examples of such polyamines are 1,2,4-triaminobenzene, 1,3,5-triaminobenzene, 2,4,6-triaminotoluene, 2,4,6-triamino-1,3,5-trimethylbenzene, 1,3,7-triaminonaphthalene, 2,4,4'-triaminobiphenyl, 2,4,6-triaminopyridine, 2,4,4'-triaminodiphenyl oxide, 2,4,4'-triaminodiphenylmethane, 2,4,4'-triaminodiphenylsulfone, 2,4,4'-triaminobenzophenone, 2,4,4'-triamino-3-methyldiphenylmethane, N,N,N-tris(4-aminophenyl)-amine, tris-(4-aminophenyl)-methane, 4,4',4''-triaminotriphenyl orthophsophate, tris-(4-aminophenyl)-phosphine oxide, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diaminobenzidine, 3,3',4,4'-tetraaminodiphenyl oxide, 3,3',4,4'-tetraaminodiphenylmethane, 3,3',4,4'-tetraaminodiphenylsulfone, 3,5-bis-(3,4-diaminophenyl)-pyridine and the oligomers of the average formula:

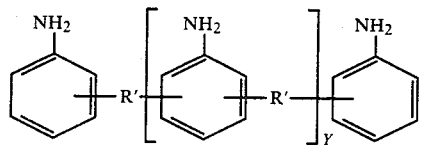

in which y represents a mean number ranging from about 0.1 to 2, the symbol R' denoting a divalent hydrocarbon group which has from 1 to 8 carbon atoms and is derived from an aldehyde or ketone of the formula:

O=R' in which the oxygen atom is bonded to a carbon atom of the radical R'; typical aldehydes and ketones are formaldehyde, acetaldehyde, enanthaldehyde, benzaldehyde, acetone, methyl ethyl ketone, hexan-2-one, cyclohexanone and acetophenone. These oligomers containing amino groups can be obtained in accordance with known processes, such as those described in French Pat. Nos. 1,430,977, 1,481,935 and 1,533,696 the disclosure of which is hereby expressly incorporated by reference and relied upon; the crude mixtures of polyamines obtained in accordance with these processes can be enriched in one or more constituents, for example, by distillation under reduced pressure.

Among the monoamines of the formula (III), namely, those amines in which n=1, alkylamines, in particular butylamine, and arylamines, in particular aniline and mesidine (or 2,4,6-trimethyl-1-aminobenzene), toluidine and ortho-, meta- and para-chloroanilines, are noted as illustrative.

In the process of the invention, the proportions of acid ($\alpha$) and salt ($\beta$) can vary over wide limits; the molar ratio of acid ($\alpha$)/salt ($\beta$) is generally between 0.01 and 100, and preferably between 0.1 and 10.

Furthermore, the following ratios are defined:

$$r_1 = \frac{\text{total number of mols of acid } (\alpha) \text{ and salts } (\beta)}{\text{total number of NH}_2 \text{ groups in the amine of the formula (III) employed in the reaction}}$$

$$r_2 = \frac{\text{total number of mols of anhydride of the formula (II) employed in the reaction}}{\text{total number of NH}_2 \text{ groups in the amine of the formula (III) employed in the reaction}}$$

In general terms, it is advantageous to comply with the following conditions:
  $r_1$ is between 0.01 and 2, and preferably between 0.1 and 1, and
  $r_2$ is between 1 and 3, and preferably between 1.01 and 1.5.

If the process of the invention is carried out continuously, the number of mols of reactants and of constituents of the catalyst system which are to be taken into consideration are obviously the number of mols employed per unit time (namely, mean number of mols).

The reaction according to the invention is carried out in the liquid phase at temperatures which are generally between 80° and 180° C., and preferably between 100° and 150° C. The lower temperatures are of little value because the reaction is slow and the higher temperatures are likely to give rise to secondary reactions.

The process according to the invention can be carried out without solvent, i.e., either in the molten state or in the form of a solution in the reactants in the case where the latter are liquid under the operating conditions.

However, in accordance with a preferred process embodiment, the reaction is carried out in an organic solvent medium, the overall concentration of reactants and catalyst system generally being between 5 and 50%, and preferably between 10 and 40% (by weight).

Solvents which advantageously are utilized are liquid and inert under the process operating conditions, that is to say, they do not react to any appreciable extent with either the anhydride of the formula (II) or the amine of the formula (III). The following are thus mentioned as illustrative: aliphatic or aromatic hydrocarbons, such as benzene, toluene, xylenes and ethylbenzene, aliphatic or aromatic hydrocarbons which are substituted by chlorine atoms, in particular chlorobenzene, methylene chloride, carbon tetrachloride, 1,2-dichloroethane and 1,1,2,2-tetrachloroethane, or which are substituted by other functional groups, such as benzonitrile, propionitrile, butyronitrile and ketones, polar aprotic solvents such as dimethylformamide and dimethylsulfoxide, and ethers such as diisobutyl ether, dimethoxyethane, diglyme (or diethylene glycol dimethyl ether) and anisole (or methoxybenzene).

From a practical point of view, various methods of operation can be adopted. In accordance with a simple method of operation, all of the reactants and catalysts are brought together in the reactor and heated to appropriate temperature. In accordance with another method of operation, which has the advantage in that it avoids secondary reactions as much as is possible, all or part of the anhydride of the formula (II) and of the catalyst system ($\alpha$)/($\beta$) are first introduced into the reactor and the amine of the formula (III) is then gradually introduced into the said reactor.

In accordance with a preferred method of operation, and with a view towards improving yields, the water is continuously removed from the reaction medium as it is formed. A convenient method for removing this water consists of continuously distilling the reaction medium, in condensing the distillate by cooling, in decanting this distillate which has condensed into two phases, one being aqueous and the other being essentially composed of the organic solvent used, in separating and removing the aqueous phase and in returning the organic phase to the top of the column.

At completion of the reaction, the oligo-imide of the formula (I), which is a product of the reaction, is separated by any known means. For example, it is possible to evaporate off the solvent and then carry out selective extractions using suitable solvents.

In accordance with an advantageous method, the process for the preparation of imide according to the invention is carried out in a solvent which is such that, at ambient temperature or at a lower temperature, the reactants and the catalyst system remain soluble (for the major part) whereas the oligoimide is insoluble or at least is only slightly soluble (solubility preferably less than 5%). Under these conditions, the oligo-imide is isolated by simply cooling the reaction medium and filtering off the precipitate obtained; the filtrate, or mother liquors, contains solvent, the catalyst system and, possibly, excess anhydride which has not reacted and a small amount of oligo-imide which has not precipitated. This mixture can be re-used, as is, in order to form the basis for a new operation, i.e., it suffices to add the anhydride of the formula (II) to this mixture, to heat the entire mass to the desired temperature and then to gradually add the amine of the formula (III) under the aforesaid typical conditions.

The reaction times in the process of the invention can obviously vary over wide limits and depend especially on the temperature used; most frequently, same are between 0.3 and 5 hours, and, more particularly, are between 0.5 and 2 hours.

The process of the invention is particularly advantageous because of the ease with which it is carried out and the good performance which can thereby be achieved, as regards both the reaction rate and the yield of oligo-imide produced.

The oligo-imides of formula (I) obtained according to the invention are used, e.g., for the preparation of thermosetting resins. By reacting oligo-imides containing several imide functions (optionally in association with monoimides) with polyamines, the oligo-imides lead, in particular, to cross-linked polymers of high heat stability (French Pat. No. 1,555,564, hereby also expressly incorporated by reference).

The above process has been described using, as the starting materials, reactants consisting of anhydrides and amines. In fact, it is known that an anhydride and a primary amine condense rapidly and without difficulty to give an amic acid of formula (IX) in accordance with the equation:

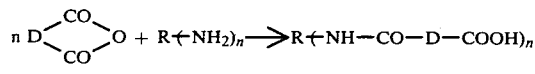

II        III        IX

Accordingly, the formation of an oligo-imide of formula I normally takes place in two stages, one being the condensation of the reactants to yield an amic acid and the other being the cyclic dehydration of the amic acid to yield an imide according to the equation:

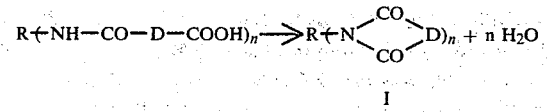

I

Therefore, it would not be outside the scope of the invention to first produce the amic acid of formula IX from an anhydride of formula (II) and an amine of formula (III) without a catalyst, and then, when this amic acid has been formed, to bring the catalyst system $(\alpha)/(\beta)$ together therewith, under the operating conditions defined above. A process of this kind can therefore be considered to be a simple variant of the general process described above, which variant, on the one hand, consists in replacing the anhydride and the amine with the amic acid, or which, on the other hand, consists in not introducing the catalyst system initially, but rather introducing same after the anhydride and the amine have begun to react.

If an amic acid of formula IX is used as starting material, the above mentioned ratio $r_1$, which suitably is between 0.01 and 2, preferably between 0.1 and 1, is defined as follows:

$$r_1 = \frac{\text{total number of mols of acid } (\alpha) \text{ and salts } (\beta)}{\text{total number of functional groups of amic acid formula (IX) employed in the reaction}}$$

In order to further illustrate the present invention and the advantages thereof, the following specific examples are given, it being understood that same are intended only as illustrative, and in nowise limitative. These examples illustrate the preparation of an imide using, as the starting material, an amic acid.

EXAMPLE 1

Into a 250 cm³ round bottomed flask equipped with a stirrer and a distillation column were introduced:

| | | |
|---|---|---|
| p-toluene sulfonic acid (1H₂O) | 0.098 g | (0.56 mM) |
| 1-methylpyridinium p-toluene sulfonate: | 0.505 g | (2.01 mM) |
| chlorobenzene | 160 g | |

(mM is an abbreviation for millimols)

The mixture was distilled at 132° C., the water being removed and the organic phase of the condensed distillate being recycled. 1.083 g (5.28 millimols) of N-(paratolyl)-maleamic acid were then added. The distillation operation at 132° C. was then repeated and the water produced by the reaction was removed. After 2 hours, the reaction was interrupted and the solution was analyzed by polarography. It was found that all the maleamic acid had been converted and that 4.64 millimols of N-tolyl-maleimide had been produced. (The chemical yield relative to reacted maleamic acid was 88%)

EXAMPLE 2

In the apparatus described in Example 1, the same operation was repeated, but using the following amounts: 0.088 g (0.5 mM) of p-toluenesulfonic acid (1H₂O), 0.868 g (2 mM) of methyltriphenylphosphonium p-toluenesulfonate, and 158 g of chlorobenzene.

The mixture was distilled at 132° C., the water being removed and the organic phase of the condensed distillate being recycled. 1.025 g (5 millimols) of N-(para-tolyl)-maleamic acid were then added. The distillation operation at 132° C. was then repeated and the water produced by the reaction was removed. After 2 hours, the reaction was interrupted and the solution was analyzed by polarography. It was found that all the maleamic acid had been converted and that 5 millimols of N-tolylmaleimide had been produced. (The chemical yield relative to reacted maleamic acid was 100%).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of an oligo-imide comprising reacting a dicarboxylic acid anhydride with an amine, the improvement which comprises conducting said reaction in the presence of a catalyst system comprising a mixture of a compound ($\alpha$) and a compound ($\beta$), ($\alpha$) being a strong inorganic or organic oxygen-containing acid, said acid bearing at least one acid functionality having an ionization constant in water which is not greater than 3, and ($\beta$) being a salt of such acid, with an organic cation selected from the group consisting of pyridinium nucleus cations, quaternary phosphonium cations and tertiary sulfonium cations.

2. The process as defined by claim 1, wherein said anhydride has the formula:

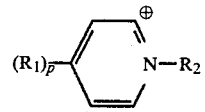  [II]

and said amine has the formula:

R$\pm$NH$_2$)$_n$  (III)

in which formulae n is a positive integer which is less than or equal to 5, R is an hydrocarbon or heterohydrocarbon radical of valency n, containing up to 50 carbon atoms, and D represents a divalent group selected from the group comprising

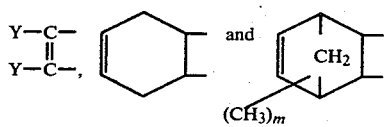

in which m is equal to 0 or 1 and Y represents hydrogen, chlorine or methyl.

3. The process as defined by claim 2, wherein said acid is selected from the group consisting of sulfuric, phosphoric, organo-sulfonic, organo-phosphonic and halogen-containing carboxylic acids.

4. The process as defined by claim 3, wherein said acid is methanesulfonic acid, para-toluenesulfonic acid or benzenesulfonic acid.

5. The process as defined by claim 1, wherein said cation in the salt ($\beta$) is a pyridinium cation having the formula

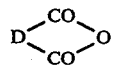 (IV)

wherein the substituents $R_1$ are the same or different from each other and represent:
a straight or branched alkyl group containing 1 to about 20 carbon atoms which is unsubstituted or substituted by a halogen atom, nitro, or alkoxy containing 1 to 5 carbon atoms;
alkoxy containing 1 to 5 carbon atoms;
a straight or branched alkenyl group containing 2 to 20 carbon atoms and 1 to 10 ethylenic double bonds which is unsubstituted or substituted by alkoxy groups containing 1 to 5 carbon atms;
a cycloalkyl- or cycloalkenyl group containing 5 to 8 carbon atoms and 0 to 2 ethylenic double bonds which is unsubstituted or substituted by 1 to 3 alkyl or alkoxy groups containing 1 to 5 carbon atoms;
an aryl group having from 6 to 12 carbon atoms which is unsubstituted or substituted by 1 to 3 alkyl or alkoxy groups containing 1 to 5 carbon atoms;
an arylalkyl group containing 1 to 5 carbon atoms in its alkyl moiety and 1 or 2 benzene nuclei which are non-fused or fused and wherein the aryl moiety is unsubstituted or substituted by 1 to 3 alkyl or alkoxy groups containing 1 to 5 carbon atoms;
a halogen atom;
a functional group selected from the group comprising hydroxyl, cyano, nitro, carboxy, loweralkylcarbonyloxy, loweralkylcarbonyl and loweracyl;
p represents an integer of from 0 to 5; or
one or two pairs of substituents $R_1$ which are in ortho position to each other together form 1 or 2 unsaturated divalent groups;
$R_2$ represents:
hydrogen;
an alkyl-, alkoxy-, alkenyl-, cycloalkyl-, cycloalkenyl-, aryl- or arylalkyl group as defined in the definition of $R_1$; or
a functional group as defined in the definition of $R_1$.

6. The process as defined in claim 5, wherein the pyridinium cation is a quarternary pyridinium cation.

7. The process as defined by claim 1 wherein said cation in the salt ($\beta$) is a phosphonium cation having the formula

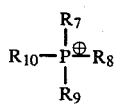

wherein:
$R_7$, $R_8$, $R_9$, and $R_{10}$ are the same or different from each other and each represent
a straight or branched alkyl group containing 1 to about 20 carbon atoms which is unsubstituted or substituted by a halogen atom, nitro, or alkoxy containing 1 to 5 carbon atoms;
alkoxy containing 1 to 5 carbon atoms;
a straight or branched alkenyl group containing 2 to 20 carbon atoms and 1 to 10 ethylenic double bonds which is unsubstitued or substituted by alkoxy groups containing 1 to 5 carbon atoms;

a cycloalkyl- or cycloalkenyl group containing 5 to 8 carbon atoms and 0 to 2 ethylenic double bonds which is unsubstituted or substituted by 1 to 3 alkyl or alkoxy groups containing 1 to 5 carbon atoms;

an aryl group having from 6 to 12 carbon atoms which is unsubstituted or substituted by 1 to 3 alkyl or alkoxy groups containing 1 to 5 carbon atoms;

an arylalkyl group containing 1 to 5 carbon atoms in its alkyl moiety and 1 or 2 benzene nuclei which are non-fused or fused and wherein the aryl moiety is unsubstituted or substituted by 1 to 3 alkyl or alkoxy groups containing 1 to 5 carbon atoms; or two of the substituents $R_7$, $R_8$, $R_9$ and $R_{10}$ together form a single divalent substituent which is an alkylene or alkenylene group containing 4 to 6 carbon atoms and 0 to 2 ethylenic double bonds which is unsubstituted or substituted by 1 to 3 alkyl or alkoxy groups containing 1 to 5 carbon atoms.

8. The process as defined by claim 1, wherein said cation in the salt ($\beta$) is a sulfonium cation having the formula

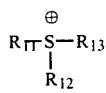

wherein:
$R_{11}$, $R_{12}$ and $R_{13}$ are the same or different from each other and each represent a straight or branched alkyl group containing 1 to about 20 carbon atoms which is unsubstituted or substituted by a halogen atom, nitro, or alkoxy containing 1 to 5 carbon atoms;

alkoxy containing 1 to 5 carbon atoms;

a straight or branched alkenyl group containing 2 to 20 carbon atoms and 1 to 10 ethylenic double bonds which is unsubstituted or substituted by alkoxy groups containg 1 to 5 carbon atoms;

a cycloalkyl- or cycloalcenyl group containing 5 to 8 carbon atoms and 0 to 2 ethylenic double bonds which is unsubstituted or substituted by 1 to 3 alkyl or alkoxy groups containing 1 to 5 carbon atoms;

an aryl group having from 6 to 12 carbon atoms which is unsubstituted or substituted by 1 to 3 alkyl or alkoxy groups containing 1 to −5 carbon atoms;

an arylalkyl group containing 1 to 5 carbon atoms in its alkyl moiety and 1 or 2 benzene nuclei which are non-fused or fused and wherein the aryl moiety is unsubstituted or substituted by 1 to 3 alkyl or alkoxy groups containing 1 to 5 carbon atoms; or two of the substituents $R_{11}$, $R_{12}$ and $R_{13}$ together form a single divalent substituent which is an alkylene group containing 4 to 8 carbon atoms or an alkenylene group containing 4 to 8 carbon atoms and one or more ethylenic double bonds, or the three substituents $R_{11}$, $R_{12}$ and $R_{13}$ together form a trivalent substituent comprising 4 to 10 carbon atoms which is saturated or is unsaturated and comprises one or more ethylenic double bonds.

9. The process as defined by claim 1, wherein the anhydride is maleic anhydride and the amine is 4,4'-diaminodiphenylmethane, or 4,4'-diaminodiphenyl ether, or 4,4'-diaminodiphenylsulfone or a toluidine.

10. The process as defined by claim 1, wherein the temperature of reaction is between about 80° and about 180° C., and the reaction is conducted in a solvent medium such that water of reaction is removed as it is formed.

11. The process as defined by claim 10 wherein the reaction temperature is between about 100° and about 150° C.

12. The process as defined by claim 1, wherein at least a portion of the anhydride of formula (II) and the amine of formula (III) are replaced by an amic acid of the formula IX:

$$R+NH-CO-D-COOH)_n \qquad (IX)$$

wherein n is a positive integer which is less than or equal to 5, R is an hydrocarbon or heterohydrocarbon radical of valency n, containing up to 50 carbon atoms, and D represents a divalent radical selected from the group comprising

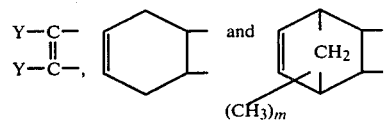

in which m is equal to 0 or 1 and Y represents hydrogen, chlorine or methyl.

13. The process as defined by claim 1, wherein the molar ratio of acid ($\alpha$) salt ($\beta$) is between 0.01 and 100, the ratio of the number of mols of acid ($\alpha$) and salt ($\beta$) to the number of NH$_2$ groups in the amine of the formula (III) is between 0.01 and 2, and the ratio of the number of mols of anhydride of the formula (II) to the number of NH$_2$ groups in the amine of the formula (III) is between 1 and 3.

14. The process as defined by claim 13, said molar ratio of acid ($\alpha$)/salt ($\beta$) being between 0.01 and 10, the ratio of number of mols acid and salt to the number of NH$_2$ groups in the amine being between 0.1 and 1, and the ratio of the number of mols of anhydride to the number of NH$_2$ groups in the amine being between 1.01 and 1.5.

15. The process as defined by claim 12, wherein the molar ratio of acid ($\alpha$) salt ($\beta$) is between 0.01 and 100, and the ratio of the number of mols of acid ($\alpha$) and salt ($\beta$) to the number of amic functional groups in the amic acid of the formula (IX) is between 0.01 and 2.

16. The process as defined by claim 15, said molar ratio of acid ($\alpha$)/salt ($\beta$) being between 0.01 and 10, and the ratio of number of mols acid ($\alpha$) and salt ($\beta$) to the number of amic functional groups in the amic acid of formula (IX) being between 0.1 and 1.

17. The process as defined by claim 3, wherein said cation is selected from the group consisting of 1-methylpyridinium, 1-methyl-2-vinylpyridinium, 1-methyl-3-hydroxypyridinium, 1-methyl-4-cyanopyridinium, 1-methyl-3,5-dichloropyridinium, 1,2,5-trimethylpyridinium, 1,2,4,6-tetramethylpyridinium, 1-ethylpyridinium, 1-ethyl-2-vinylpyridinium, 1-ethyl-2-ethoxypyridinium, 1,4-diethylpyridinium, 1-methyl-4-acetylpyridinium, 1-propylpyridinium, 1-propyl-4-phenylpyridinium, 1-butylpyridinium, 1-butyl-2,4-dimethylpyridinium, 1-butyl-2-vinylpyridinium, 1-methoxypyridinium, 1,4-dimethoxypyridinium, 1,3,5-trimethoxypyridinium, 1-vinylpyridinium, 1-phenylpyridinium, 1-benzylpyridinium, 1-benzyl-3-carboxypyridinium, 1-(p-methylbenzyl)pyridinium, 1-benzyl-3,5-dimethylpyridinium, 1-methylquinolinium, 1-ethylquinolinium, 1-vinylquinolinium, 1-allylquinolinium, tetramethylphosphonium, tetraethylphosphonium, tetrapropylphosphonium, tetrabutylphosphonium, tetra(chloromethyl) phosphonium, tetraphenylphosphonium, tetrabenzylphosphonium, trimethylethylphosphonium, trimethylphenylphosphonium, trimethylbenzylphosphonium, triethylvinylphosphonium, triethylpropylphosphonium, triethyldecylphosphonium, tripropylethylphosphonium, tripropylphenylphosphonium, tributylethylphosphonium, triphenylmethylphosphonium, triphenylethylphosphonium, triphenylpropylphosphonium, triphenylbutylphosphonium, triphenylbenzylphosphonium, tribenzylethylphosphonium, tri(p-methylphenyl)methylphosphonium, dimethylethylphenylphosphonium, dimethyloctylbenzylphosphonium, diethylmethylphenylphosphonium, dipropylmethylphenylphosphonium, dimethyldiethylphosphonium, dimethyldiphenylphosphonium, diethyldiphenylphosphonium, methylethylisopropylisobutylphosphonium, methylethylphenylbenzylphosphonium, phenylethyltetramethylenephosphonium, phenylpropyltetramethylenephosphonium, phenylethylpentamethylenephosphonium, trimethylsulfonium, triethylsulfonium, tripropylsulfonium, tributylsulfonium, triphenylsulfonium, tri(2-chloro-ethyl)sulfonium, dimethylvinylsulfonium, dimethylallylsulfonium, dimethylbutylsulfonium, dimethylphenylsulfonium, dimethylbenzylsulfonium, diethylmethylsulfonium, diethylpropylsulfonium, diethylphenylsulfonium, dibutylbenzylsulfonium, dimethylcyclohexylsulfonium, diphenylmethylsulfonium, diphenylethylsulfonium, diphenylallylsulfonium, methylethylphenylsulfonium, methylethylbenzylsulfonium and methoxymethylphenylsulfonium.

18. The process as defined by claim 17, wherein said acid is selected from the group consisting of methanesulfonic acid, para-toluenesulfonic acid and benzenesulfonic acid.

* * * * *